US012750637B2

(12) United States Patent
Hanson et al.

(10) Patent No.: US 12,750,637 B2
(45) Date of Patent: Sep. 29, 2026

(54) SYSTEMS AND METHODS FOR ESTABLISHING MONITORED INDIVIDUAL LOCATION VIA A TRACKING DEVICE ASSOCIATED WITH THE MONITORED INDIVIDUAL USING INTERMITTENT, MOBILE CONNECTION TO NON-ASSOCIATED DEVICES

(71) Applicant: BI Incorporated, Boulder, CO (US)

(72) Inventors: Duke Hanson, Boulder, CO (US); Ric Miller, Boulder, CO (US); Todd Bischoff, Boulder, CO (US)

(73) Assignee: BI Incorporated, Boulder, CO (US)

( * ) Notice: Subject to any disclaimer, the term of this patent is extended or adjusted under 35 U.S.C. 154(b) by 321 days.

(21) Appl. No.: 18/481,496

(22) Filed: Oct. 5, 2023

(65) Prior Publication Data

US 2024/0298147 A1 Sep. 5, 2024

Related U.S. Application Data

(60) Provisional application No. 63/449,919, filed on Mar. 3, 2023.

(51) Int. Cl.
*H04W 4/029* (2018.01)
*A61B 5/00* (2006.01)
*A61B 5/11* (2006.01)

(52) U.S. Cl.
CPC ........... *H04W 4/029* (2018.02); *A61B 5/1112* (2013.01); *A61B 5/681* (2013.01); *A61B 5/6898* (2013.01)

(58) Field of Classification Search
CPC ..... H04W 12/02; H04W 12/06; H04W 4/029; H04W 4/023; H04W 4/027; H04W 12/104; H04W 12/63; H04W 48/04; H04W 64/003
USPC ........................... 455/456.1, 419, 435.1, 442
See application file for complete search history.

(56) References Cited

U.S. PATENT DOCUMENTS

| | | | | |
|---|---|---|---|---|
| 11,281,971 B2 * | 3/2022 | Busch | G06V 20/52 | |
| 11,502,551 B2 * | 11/2022 | Leabman | H02J 50/20 | |
| 2004/0260463 A1 * | 12/2004 | Hathiram | G08B 21/0202 | 701/519 |
| 2006/0236143 A1 * | 10/2006 | Kidoguchi | G06F 1/3203 | 713/320 |
| 2007/0162674 A1 * | 7/2007 | Leichsenring | G06F 21/62 | 710/241 |
| 2009/0013064 A1 * | 1/2009 | Taylor | H04L 41/082 | 709/223 |
| 2015/0364027 A1 * | 12/2015 | Haupt | G08B 25/08 | 340/521 |
| 2020/0242471 A1 * | 7/2020 | Busch | G06V 10/764 | |
| 2022/0045554 A1 * | 2/2022 | Leabman | H02J 50/20 | |

FOREIGN PATENT DOCUMENTS

| | | | |
|---|---|---|---|
| WO | WO-2023007477 A2 * | 2/2023 | G06F 9/4555 |
| WO | WO-2025262680 A1 * | 12/2025 | H04L 67/1014 |

* cited by examiner

*Primary Examiner* — Joseph Arevalo
(74) *Attorney, Agent, or Firm* — Osha Bergman Watanabe & Burton LLP

(57) ABSTRACT

Various embodiments provide systems and methods for locating a tracking device involving selective use of non-associated devices.

20 Claims, 10 Drawing Sheets

SYSTEMS AND METHODS FOR ESTABLISHING MONITORED INDIVIDUAL LOCATION VIA A TRACKING DEVICE ASSOCIATED WITH THE MONITORED INDIVIDUAL USING INTERMITTENT, MOBILE CONNECTION TO NON-ASSOCIATED DEVICES

CROSS REFERENCE TO RELATED APPLICATIONS

The present application claims priority to (is a non-provisional application of) U.S. Pat. App. No. 63/449,919 entitled "Systems and Methods for Using Intermittent, Mobile Source Location Derived from Devices Not Associated with a Tracked Device and/or Tracked Individual to Define Location and Movement of the Tracked Individual", and filed Mar. 3, 2023 by Hanson et al. The entirety of the aforementioned reference is incorporated herein by reference for all purposes.

BACKGROUND OF THE INVENTION

Various embodiments provide systems and methods for locating a tracking device, and more particularly to systems and methods for locating a tracking device involving selective use of non-associated devices.

Tracking devices have been attached to monitored individuals and provide an ability to automatically determine the location of the respective monitored individual. Such tracking devices can include, for example, location determination circuitry that depends upon, for example, signal reception from location satellites, WiFi devices, and/or transmitting beacons. Each of these types of location services use differing levels of power to establish a location of a tracking device. Where power is depleted to a defined extent, such location determination circuitry can fail causing a loss of location information from the tracking device.

Thus, for at least the aforementioned reasons, there exists a need in the art for more advanced approaches, devices and systems for detecting monitored individual location.

BRIEF SUMMARY OF THE INVENTION

Various embodiments provide systems and methods for locating a tracking device involving selective use of non-associated devices.

This summary provides only a general outline of some embodiments. Many other objects, features, advantages and other embodiments will become more fully apparent from the following detailed description, the appended claims and the accompanying drawings and figures.

BRIEF DESCRIPTION OF THE DRAWINGS

A further understanding of the various embodiments may be realized by reference to the figures which are described in remaining portions of the specification. In the figures, similar reference numerals are used throughout several drawings to refer to similar components. In some instances, a sub-label consisting of a lower-case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Figure 1A:
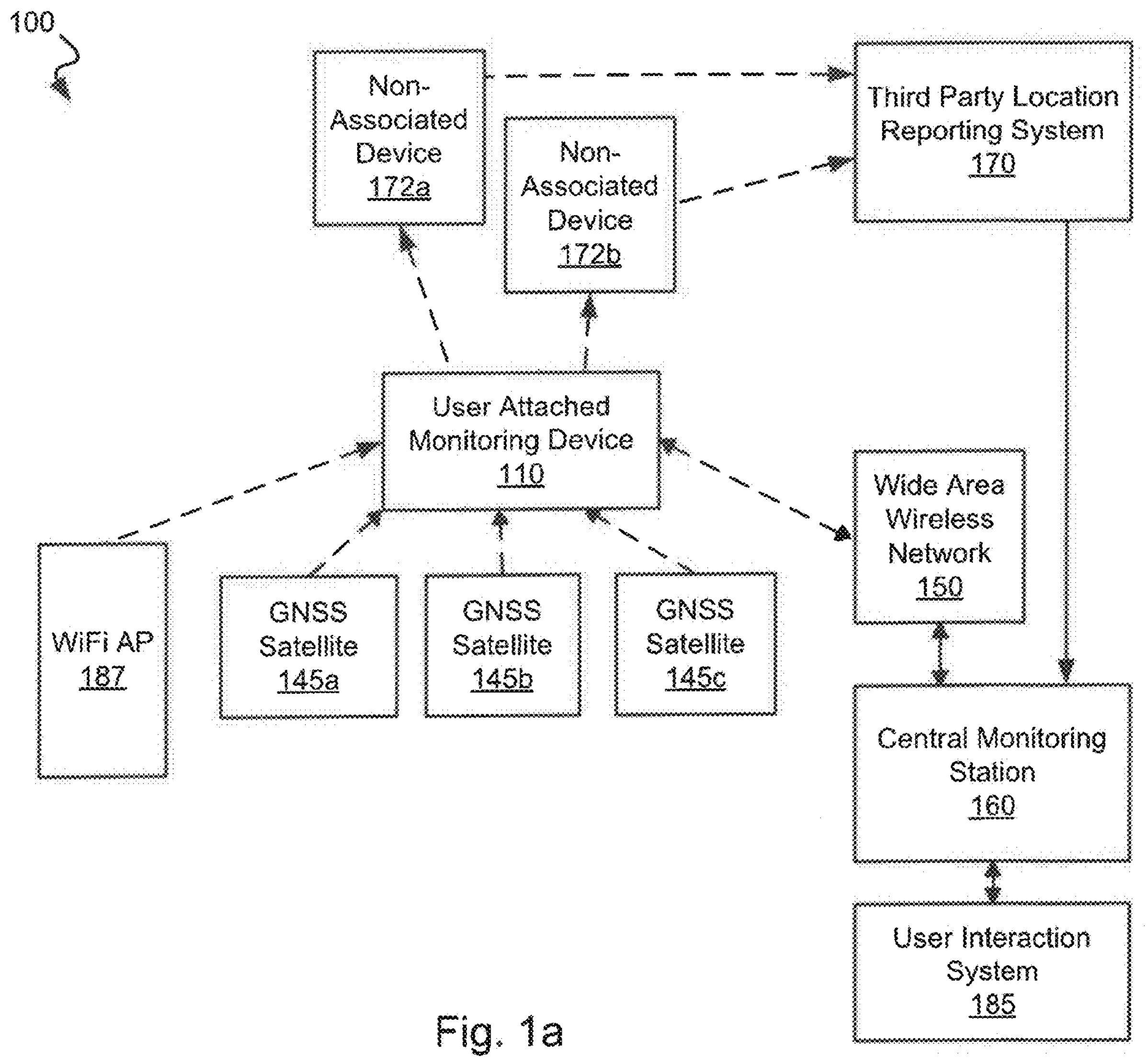
FIG. 1*a*-1*d* are block diagrams illustrating a location monitoring system that includes a user attached monitoring device having WiFi access point-based location determination circuitry, satellite-based location determination circuitry, and non-associated device-based location determination circuitry in accordance with various embodiments.

Various embodiments provide systems and methods for locating a tracking device involving selective use of non-associated devices.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "cell" includes reference to one or more of such cells.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the elements shown in the flowchart may be omitted, repeated, and/or performed in a different order than the order shown. Accordingly, the scope disclosed herein should not be considered limited to the specific arrangement of steps shown in the flowchart.

Although multiple dependent claims are not introduced, it would be apparent to one of ordinary skill that the subject matter of the dependent claims of one or more embodiments may be combined with other dependent claims.

In the following description of FIGS. 1-7, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

As used herein, the term "non-associated device" means any device that is not controlled by a monitoring device or an individual associated with the monitoring device and capable of transmitting its location information to a third-party location reporting system. Such a third-party location reporting system may be a crowd sourced location system as are known in the art. As an example, a third-party location reporting system may be the crowd sourced location system provided by Apple™. Non-associated devices may be, but are not limited to, mobile telephones, smart watches, or the like that are registered to provide location information to a third-party location reporting system. Based upon the disclosure provided herein, one of ordinary skill in the art will recognize a variety of devices that may be used as non-associated devices, and a variety of systems that may include both non-associated devices and a third-party reporting system used for identifying the location of a monitoring device that has provided identifications to one or more non-associated devices.

Various embodiments provide a wrist-worn impairment detection monitor. In some cases, such a wrist-worn impairment detection monitor is capable of rendering a likelihood that a wearer of the wrist-worn impairment detection monitor is impaired. The wrist-worn impairment detection monitoring has a variety of input sensors that can be used in relation to impairment detection processing capabilities to determine an impairment status of an individual.

Various embodiments provide methods for tracking a monitoring device that include: monitoring an operational status of the monitoring device to yield at least a first operational status of the monitoring device; based at least in part on the first operational status of the monitoring device, enabling a non-associated device-based location processing in the monitoring device. The non-associated device-based location processing includes communicating a data set identifying the monitoring device to a non-associated device within communication range of the monitoring device. In such a case, the location of the non-associated device is used as a proxy for the location of the monitoring device. In some instances of the aforementioned embodiments, the non-associated device is a mobile phone associated with a third-party location service.

In various instances of the aforementioned embodiments, the monitoring device is a user attached monitoring device including a securing mechanism configured to secure the user attached monitoring device to a monitored individual. In some instances of the aforementioned embodiments, the monitoring device is a user attached monitoring device, and the user attached monitoring device is configured to perform direct location processing. Such direct location processing is selected from one or more of: satellite-based location processing, and WiFi based location processing. In some such instances, the methods further include: based at least in part on the first operational status of the monitoring device, disabling the direct location processing.

In some instances of the aforementioned embodiments, the first operational status of the monitoring device is one of: a power status of the monitoring device, or a tamper status of the monitoring device. In various instances of the aforementioned embodiments, the first operational status of the monitoring device is a power status of the monitoring device, and enabling the non-associated device-based location processing in the monitoring device is based upon a combination of the power status of the monitoring device and a likelihood that the monitoring device is within communication range of two or more non-associated devices. In some instances of the aforementioned, the first operational status of the monitoring device is a tamper status of the monitoring device, and enabling the non-associated device-based location processing in the monitoring device is based upon a combination of the tamper status of the monitoring device and at least one of: a motion status of the monitoring device, or a biometrics status of the monitoring device. In various instances of the aforementioned embodiments, the first operational status of the monitoring device is a tamper status of the monitoring device, wherein the monitoring device is a user attached monitoring device attached to a monitored individual, and enabling the non-associated device-based location processing in the monitoring device is based upon a combination of the tamper status of the monitoring device and a communication status with a user detached monitoring device associated with the monitored individual. In some such instances the user detached monitoring device is a mobile phone.

Other embodiments provide tracking systems that include: a monitoring device associated with a monitored individual, a processor, and a computer readable medium. The monitoring device includes: a non-associated device-based location processing circuit; and a direct location processing circuit. The direct location processing circuit is one of a satellite-based location processing circuit, and/or WiFi based location processing circuit. The computer readable medium has stored therein instructions which when executed by the processor cause the processor to: monitor an operational status of the monitoring device to yield at least a first operational status of the monitoring device; based at least in part on the first operational status of the monitoring device, enable the non-associated device-based location processing circuit in the monitoring device. The non-associated device-based location processing circuit is configured to: communicate a data set identifying the monitoring device to a non-associated device within communication range of the monitoring device, and rely upon the non-associated device to report a location of the non-associated device as a location of the monitoring device to a recipient device.

Turning to FIG. 1*a*, a block diagram illustrates a monitoring system 100 including a user attached monitor device 110 and a central monitoring station 160. Central monitoring station 160 is wirelessly coupled to user attached monitor device 110 via one or more wide area wireless (e.g., cellular telephone network, Internet via a WiFi access point, or the like) communication networks 150.

Central monitoring station 160 may be any location, device or system where location data and/or other types of data are received, including by way of non-limiting example: a cellular/smart phone, an email account, a website, a network database, and a memory device. The location data and/or other types of data are stored by central monitoring station 160 and are retrievable by a monitoring individual, such as a parent, guardian, parole officer, court liaison, spouse, friend, or other authorized group or individual. In this manner, the monitoring individual is able to respond appropriately to detected activity of a monitored individual. In some cases, the monitoring individual is able to retrieve the location data and/or other data types via a user interaction system 185 which may be, but is not limited to, a network connected user interface device communicatively coupled via a network to central monitoring station 160 and/or directly to user attached monitor device 110 via wide area wireless network 150.

Central monitoring station 160 may include a server supported website, which may be supported by a server system comprising one or more physical servers, each having a processor, a memory, an operating system, input/output interfaces, and network interfaces, all known in the art, coupled to the network. The server supported website comprises one or more interactive web portals through which the monitor may monitor the location of the monitored individual in accordance with the described embodiments. In particular, the interactive web portals may enable the monitor to retrieve the location and user identification data of one or more monitored individuals, set or modify 'check-in' schedules, and/or set or modify preferences. The interactive web portals are accessible via a personal computing device, such as for example, a home computer, laptop, tablet, and/or smart phone.

In some embodiments, the server supported website comprises a mobile website or mobile application accessible via a software application on a mobile device (e.g. smart phone). The mobile website may be a modified version of the server supported website with limited or additional capabilities suited for mobile location monitoring.

User attached monitor device 110 includes a location sensor that senses the location of user attached monitor device 110 and generates corresponding location data. For example, when user attached monitor device 110 is capable of receiving wireless global navigation satellite system (hereinafter "GNSS") location information 136, 138, 139 from a sufficient number of GPS or GNSS satellites 145 respectively, user attached monitor device 110 may use the received wireless GNSS location information to calculate or otherwise determine the location of a human subject to which user attached monitor device 110 is attached. Global positioning system (hereinafter "GPS) is one example of a GNSS location system. While GPS is used in the specific embodiments discussed herein, it is recognized that GPS may be replaced by any type of GNSS system. In some instances, this location includes latitude, longitude, and elevation. It should be noted that other types of earth-based triangulation may be used in accordance with different embodiments of the present invention. For example, other cell phone-based triangulation, UHF band triangulation such as, for example, long range (hereinafter "LoRa") triangulation signals. Based on the disclosure provided herein, one of ordinary skill in the art will recognize other types of earth-based triangulation that may be used. The location data may comprise one or more of, but is not limited to: global positioning system ("GPS") data, Assisted GPS ("A-GPS") data, Advanced Forward Link Trilateration ("AFLT") data, and/or cell tower triangulation data. Where GPS is used, user attached monitor device 110 receives location information from three or more GPS or GNSS satellites 145 via respective communication links 136, 138, 139. The location data and/or other data gathered by user attached monitor device 110 is wirelessly transmitted to central monitoring station 160 via wide area wireless network 150 accessed via a wireless link 135.

Further, user attached monitor device 110 includes WiFi based location determination circuitry that is configured to communicate with one or more WiFi access points 187, and based thereon to determine location of user attached monitor device 110.

Yet further, user attached monitor device 110 includes non-associated device-based location determination circuitry that is configured to sense that one or more non-associated devices 172 (e.g., a non-associated device 172*a* and/or a non-associated device 172*b*) is/are within range of user attached monitor device 110, and to communicate (i.e., transmit) an identification of user attached monitor device 110 to the identified non-associated device. In some embodiments, the aforementioned communications are performed via BlueTooth™ or another relatively short range, low-power communication protocol. Based upon the disclosure provided herein, one of ordinary skill in the art will recognize a variety of protocols that may be used for communications between user attached monitor device 110 and a nearby non-associated device 172.

In turn, the non-associated device that received the identification information from user attached monitor device 110 reports the identification received from user attached monitor device 110 and the location of the non-associated device to a third-party location reporting system 170. Third-party location reporting system 170 in turn transfers the received identification and location information to a recipient registered with the received identification in third-party location reporting system 170. In this case, the recipient registered with the received identification in third-party location reporting system 170 is central monitoring station 160. In such a case, a location of the non-associated device that provided the identification of user attached monitor device 110 to third-party location reporting system 170 is established by central monitoring station 160 as the location of user attached monitor device 110. The power requirements of the user attached monitor device 110 for identifying the non-associated device and communicating the identification to the non-associated device are less than that required to determine location based either on WiFi access points 187 or GNSS satellites 145.

Figure 1B:
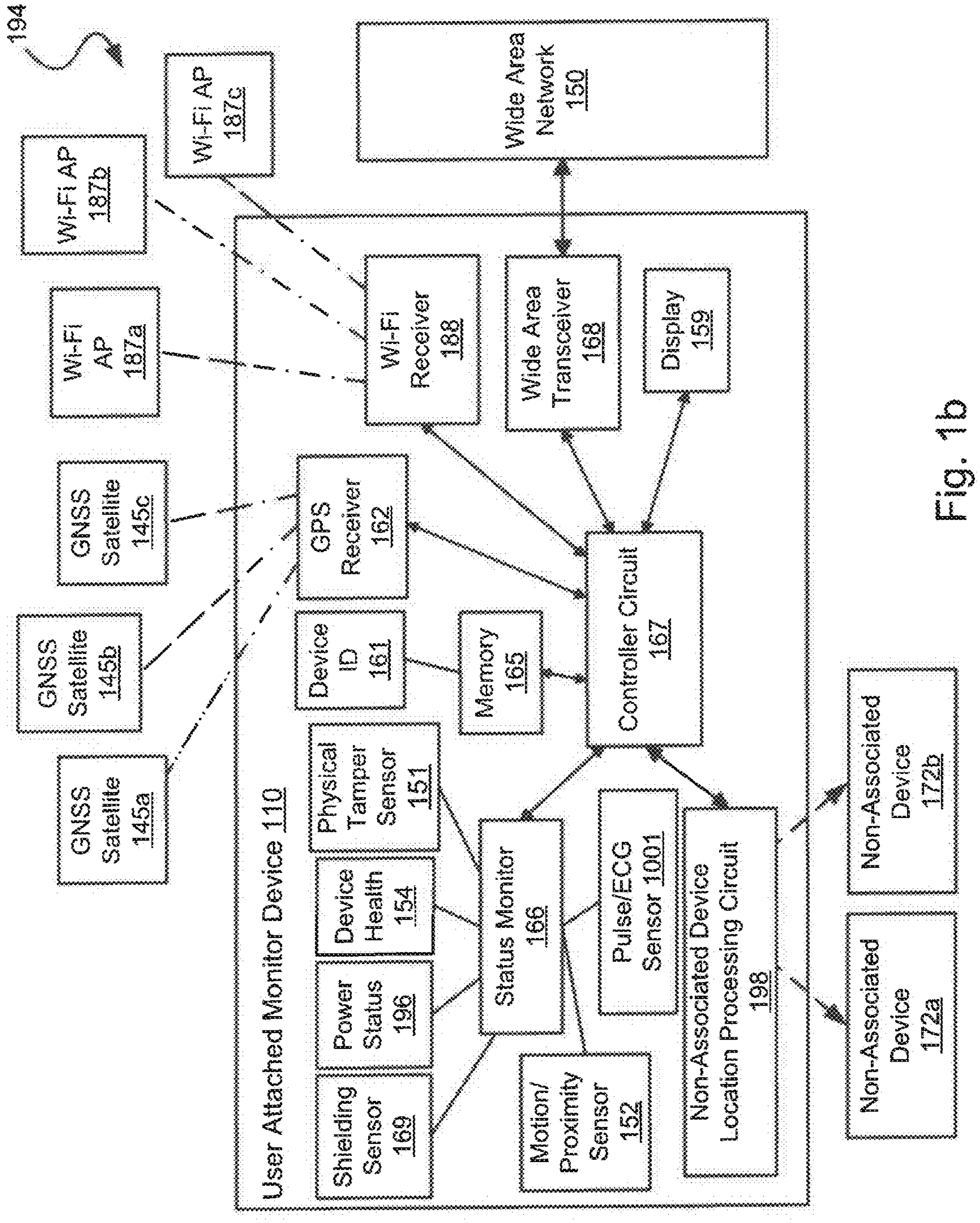

Turning to FIG. 1*b*, a block diagram 194 of user attached monitor device 110 is shown in accordance with some embodiments. As shown, user attached monitor device 110 includes a device ID 161 that may be maintained in a memory 165, and is thus accessible by a controller circuit 167. Controller circuit 167 interacts with a GPS receiver 162 and memory 165 at times for storing and generating records of successively determined GPS locations. Similarly, controller circuit 167 interacts with a WiFi receiver 188 and memory 165 at times for storing and generating records of successively determined WiFi access point identifications and signal strength. In some cases, memory 165 may include instructions (e.g., software-based or firmware-based instructions) executable by controller circuit 167 to perform and/or enable various functions associated with user attached monitor device 110. As user attached monitor device 110 comes within range of one or more WiFi access points (e.g., a WiFi access point 187*a*, a WiFi access point 187*b*, and/or a WiFi access point 187*c*), WiFi receiver 188 senses the signal provided by the respective WiFi access points, and provides an identification of the respective WiFi access point and a signal strength of the signal received from the WiFi access point to WiFi receiver 188. This information is provided to controller circuit 167 which stores the information to memory 165.

Additionally, user attached monitor device 110 includes a non-associated device location processing circuit 198. Non-associated device location processing circuit 198 is configured to sense that one or more non-associated devices 172 is/are within range of user attached monitor device 110, and to communicate (i.e., transmit) an identification of user attached monitor device 110 to the identified non-associated device. In turn, the non-associated device that received the identification information from user attached monitor device 110 reports the identification received from user attached monitor device 110 and the location of the non-associated device to third-party location reporting system 170. Third-party location reporting system 170 in turn transfers the received identification and location information to a recipient registered with the received identification in the system. In this case, the recipient registered with the received identification in the system is central monitoring station 160. The power requirements of the user attached monitor device 110 for identifying the non-associated device and communicating the identification to the non-associated device are substantially less than determining location based either on WiFi access points 187 or GNSS satellites 145.

Where user attached monitor device 110 is operating in a standard mode, controller circuit 167 causes an update and reporting of the location of user attached monitor device 110 via a wide area transceiver 168 and wide area communication network 150. In some embodiments, wide area transceiver 168 is a cellular telephone transceiver. In some cases, the location data is time stamped. In contrast, where user attached monitor device 110 is within range of a public WiFi access point, reporting the location of user attached monitor device 110 may be done via the public WiFi access point in place of the cellular communication link. In other modes triggered by conditions in user detached monitor device 110, controller circuit 167 causes non-associated device location processing circuit 198 to provide for reporting a proxy for the location of user attached monitor device 110 by transmitting its identification to any non-associated device 172 within range. In such a case, the proxy for the location is the location of the non-associated device 172 that received identification from user attached monitor device 110. Conditions for using the proxy location by communicating the identification information of user attached monitor device 110 are discussed more fully in relation to FIGS. 4-8 below.

Which technologies (e.g., GNSS and/or WiFi) are used to update the location of user attached monitor device 110 may be selected either by default, by programming from central monitor station 160, or based upon conditions detected in user attached monitor device 110 with corresponding predetermined selections. For example, it may be determined whether sufficient battery power as reported by power status 196 remains in user attached monitor device 110 to support a particular position determination technology. Where insufficient power remains, using the proxy location by communicating the identification information of user attached monitor device 110 to a non-associated device 172 may be enabled and other location technologies disabled.

In some cases, a maximum cost of resolving location may be set for user attached monitor device 110. For example, resolving WiFi location data or via a non-associated device may incur a per transaction cost to have a third-party service provider resolve the location information. When a maximum number of resolution requests have been issued, the WiFi position determination technology or the non-associated device approach may be disabled.

Further, it may be determined whether the likelihood that a particular position determination technology will be capable of providing meaningful location information. For example, where user attached monitor device 110 is moved indoors, GPS receiver 162 may be disabled to save power. Alternatively, where the tracking device is traveling at relatively high speeds, WiFi receiver 188 may be disabled. As yet another example, where cellular phone jamming is occurring, support for cell tower triangulation position determination may be disabled. As yet another example, where GPS jamming is occurring, GPS receiver 162 may be disabled. As yet another example, where user attached monitor device 110 is stationary, the lowest cost (from both a monetary and power standpoint) tracking may be enabled while all other technologies are disabled. Which position determination technologies are used may be based upon a zone in which a tracking device is located. Some zones may be rich in WiFi access points and in such zones WiFi technology may be used. Otherwise, another technology such as cell tower triangulation or GPS may be used. Based upon the disclosure provided herein, one of ordinary skill in the art will recognize other scenarios and corresponding combinations of technologies may be best.

Controller circuit 167 of user attached monitor device 110 at times functions in conjunction with wide area transceiver 168 to send and receive data and signals through wide area communication network 150. This link at times is useful for passing information and/or control signals between a central monitoring system 160 and user attached monitor device 110. The information transmitted may include, but is not limited to, location information, measured alcohol information, one or more passive or active impairment tests applied to the monitored individual, and information about the status of user attached monitor device 110. Based on the disclosure provided herein, one of ordinary skill in the art will recognize a variety of information that may be transferred via wide area communication network 150.

Various embodiments of user attached monitor device 110 include a variety of sensors capable of determining the status of user attached monitor device 110, and of the individual to which it is attached. For example, a status monitor 166 may include one or more of the following subcomponents: power status sensor 196 capable of indicating a power status of user attached monitor device 110, and/or a pulse/ECG sensor 1001 operable to sense pulse rate of the monitored individual and an electrocardiogram unique to the monitored individual based upon electrodes (not shown) in contact with the skin of the monitored individual. The power status may be expressed, for example as a percentage of battery life remaining. Based upon the disclosure provided herein, one of ordinary skill in the art will recognize a variety of forms in which power status may be expressed. The pulse rate may be expressed in beats per minute and the ECG may be shown visually via display 159. Based upon the disclosure provided herein, one of ordinary skill in the art will recognize a variety of forms in which pulse rate and/or ECG rate may be expressed.

In addition, user attached monitor device 110 includes a set of shielding sensors 169 that are capable of determining whether user attached monitor device 110 is being shielded from receiving GPS signals and/or if GPS jamming is ongoing, a set of device health indicators 154, a tamper sensor 151 capable of determining whether unauthorized access to user attached monitor device 110 has occurred or whether user attached monitor device 110 has been removed from an associated individual being monitored, and/or a motion/proximity sensor 152 capable of determining whether user attached monitor device 110 is moving and/or whether it is within proximity of an individual associated with user detached monitor device (not shown—see FIG. 3) associated with the monitored individual. In some cases, motion/proximity sensor 152 includes one or more accelerometer sensors and/or vibration gyro sensors that are capable of accurately sensing motion of the monitored individual. In addition, motion/proximity sensor 152 includes sensors capable of determining a proximity of user attached monitor device 110 to a monitored individual to which the device is assigned. This information may be used to assure that the monitored individual is wearing user attached monitor device 110. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into user attached monitor device 110 according to various different instances and/or embodiments.

In some embodiments, a user input (not shown) may be integrated into a display 159 and allows for a user of user attached monitor device 110 to provide information to user attached monitor device 110. Display 159 is communicatively coupled to controller circuit 167.

Figure 1C:
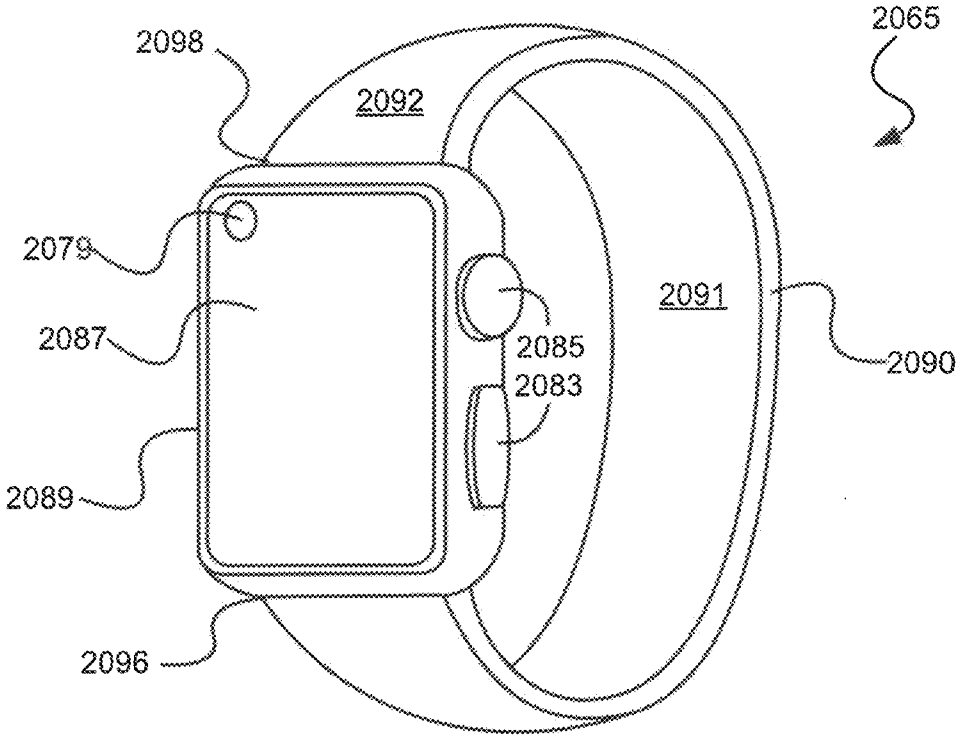

Turning to FIG. 1*c*, a user attached monitor device 2065 is shown with an example attachment element 2090 connected at opposite ends of user attached monitor device 2065 (i.e., a first end 2096 and a second end 2098). User attached monitor device 2065 is one example implementation of user attached monitor device 110 of FIGS. 1*a*-1*b*, user attached monitor device 210 of FIGS. 2*a*-2*b*, or user attached monitor device 310 of FIG. 3. Attachment element 2090 has an outer surface 2092 and an inner surface 2091. Attachment element 2090 is operable to securely attach a user attached monitor device 2065 to a limb of an individual in accordance with some embodiments. In some cases, attachment element 2090 is tailored to attach to a wrist of a monitored individual. In various embodiments, attachment element 2090 includes electrically and/or optically conductive material used to make a conductive connection from first end 2096 to second end 2098 through attachment element 2090 and is used in relation to determining whether user attached monitor device 2065 remains attached and/or has been tampered with. Thus, for example, where attachment element 2090 is cut, the conductive connection is broken indicating a tamper has occurred. While FIG. 1*c* shows a strap as an example attachment element, based upon the disclosure provided herein, one of ordinary skill in the art will recognize other types of attachment elements that may be used in relation to different embodiments. In other embodiments, attachment element 2090 is long enough to attach around the torso of the monitored individual and is sufficiently flexible to allow expansion and contraction of the chest of the monitored individual as they breath. Such expansion and contraction may be used to sense respiration rate of the monitored individual.

User attached monitor device 2065 includes a case 2089 in which various electronic components are maintained. In addition, user attached monitor device 2065 includes a button 2083, a radial dial 2085, a display 2087 (which may be a touchscreen display), and a combination speaker, microphone, and image sensor 2079. Together, user attached monitor device 2065 includes a button 2083, a radial dial 2085, a display 2087, a combination speaker, microphone, and image sensor 2079 provide the user interface for user attached monitor device 2065 and support the functionality of the various sensors discussed above in relation to FIG. 1*b*. Based upon the disclosure provided herein, one of ordinary skill in the art will recognize a variety of inputs and outputs that may be incorporated into user attached monitor device 2065 to provide the functionality discussed herein.

Figure 1D:

Turning to FIG. 1*d*, a user attached monitor device 1100 is shown with an example attachment element 1090 connected at opposite ends of a case 1089. User attached monitor device 1100 is another example implementation of user attached monitor device 110 of FIGS. 1*a*-1*b*, user attached monitor device 210 of FIGS. 2*a*-2*b*, or user attached monitor device 310 of FIG. 3. Attachment element 1090 is configured to securely attach a case 1089 to a limb of an individual in accordance with some embodiments. In various embodiments, attachment element 1090 includes electrically and/or optically conductive material used to make a conductive connection from one side of case 1089 to the opposite side of case 1089 and is used in relation to determining whether user attached monitor device 1100 remains attached and/or has been tampered with. While FIG. 1*d* shows a strap as an example attachment element, based upon the disclosure provided herein, one of ordinary skill in the art will recognize other types of attachment elements that may be used in relation to different embodiments.

Figure 2A:
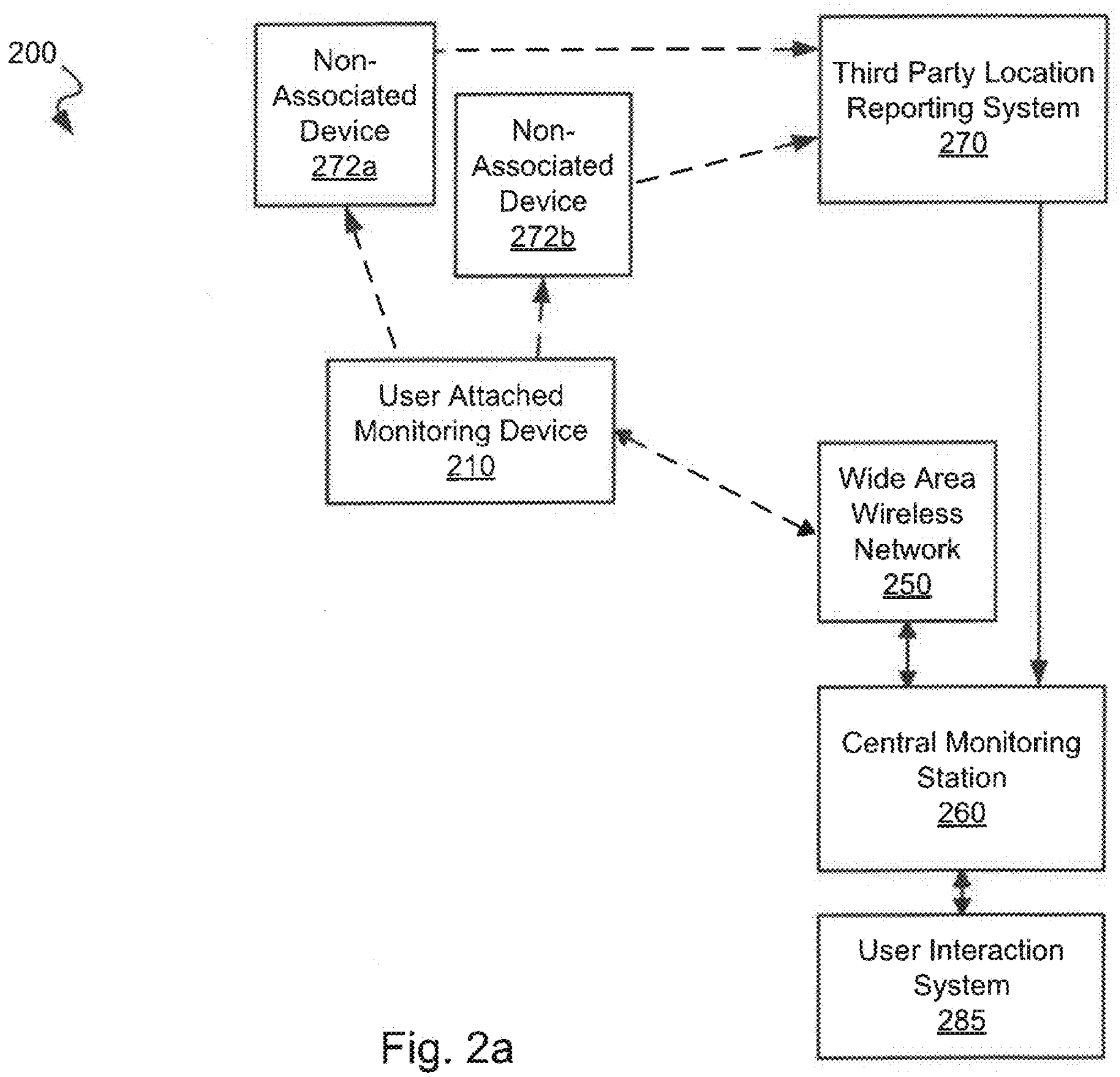
FIGS. 2*a*-2*b* are block diagrams illustrating a location monitoring system that includes only non-associated device-based location determination circuitry in accordance with some embodiments.

Turning to FIG. 2*a*, a block diagram of a location monitoring system 200 that includes only non-associated device-based location determination circuitry is shown in accordance with some embodiments. As shown, location monitoring system 200 includes a user attached monitor device 210 that is communicably coupled to a central monitoring station 260 via a wide area wireless network 250 (e.g., cellular telephone network, Internet via a WiFi access point, or the like).

Central monitoring station 260 may be any location, device or system where location data and/or other types of data are received, including by way of non-limiting example: a cellular/smart phone, an email account, a website, a network database, and a memory device. The location data and/or other types of data are stored by central monitoring station 260 and is retrievable by a monitoring individual, such as a parent, guardian, parole officer, court liaison, spouse, friend, or other authorized group or individual. In this manner, the monitoring individual is able to respond appropriately to detected activity of a monitored individual. In some cases, the monitoring individual is able to retrieve the location data and/or other data types via a user interaction system 285 which may be, but is not limited to, a network connected user interface device communicatively coupled via a network to central monitoring station 260 and/or directly to user attached monitor device 210 via wide area wireless network 250.

Central monitoring station 260 may include a server supported website, which may be supported by a server system comprising one or more physical servers, each having a processor, a memory, an operating system, input/output interfaces, and network interfaces, all known in the art, coupled to the network. The server supported website comprises one or more interactive web portals through which the monitor may monitor the location of the monitored individual in accordance with the described embodiments. In particular, the interactive web portals may enable the monitor to retrieve the location and user identification data of one or more monitored individuals, set or modify 'check-in' schedules, and/or set or modify preferences. The interactive web portals are accessible via a personal computing device, such as for example, a home computer, laptop, tablet, and/or smart phone.

In some embodiments, the server supported website comprises a mobile website or mobile application accessible via a software application on a mobile device (e.g. smart phone). The mobile website may be a modified version of the server supported website with limited or additional capabilities suited for mobile location monitoring.

User attached monitor device 210 includes non-associated device-based location determination circuitry that is configured to sense that one or more non-associated devices 272 (e.g., a non-associated device 272*a* and/or a non-associated device 272*b*) is/are within range of user attached monitor device 210, and to communicate (i.e., transmit) an identification of user attached monitor device 210 to the identified non-associated device. In some embodiments, the aforementioned communications are performed via BlueTooth™ or another relatively short range, low-power communication protocol. Based upon the disclosure provided herein, one of ordinary skill in the art will recognize a variety of protocols that may be used for communications between user attached monitor device 210 and a nearby non-associated device 272.

In turn, the non-associated device that received the identification information from user attached monitor device 210 reports the identification received from user attached monitor device 210 and the location of the non-associated device to a third-party location reporting system 270. Third-party location reporting system 270 in turn transfers the received identification and location information to a recipient registered with the received identification in third-party location reporting system 270. In this case, the recipient registered with the received identification in third-party location reporting system 270 is central monitoring station 260. In such a case, a location of the non-associated device that provided the identification of user attached monitor device 210 to third-party location reporting system 270 is established by central monitoring station 260 as the location of user attached monitor device 210.

Figure 2B:
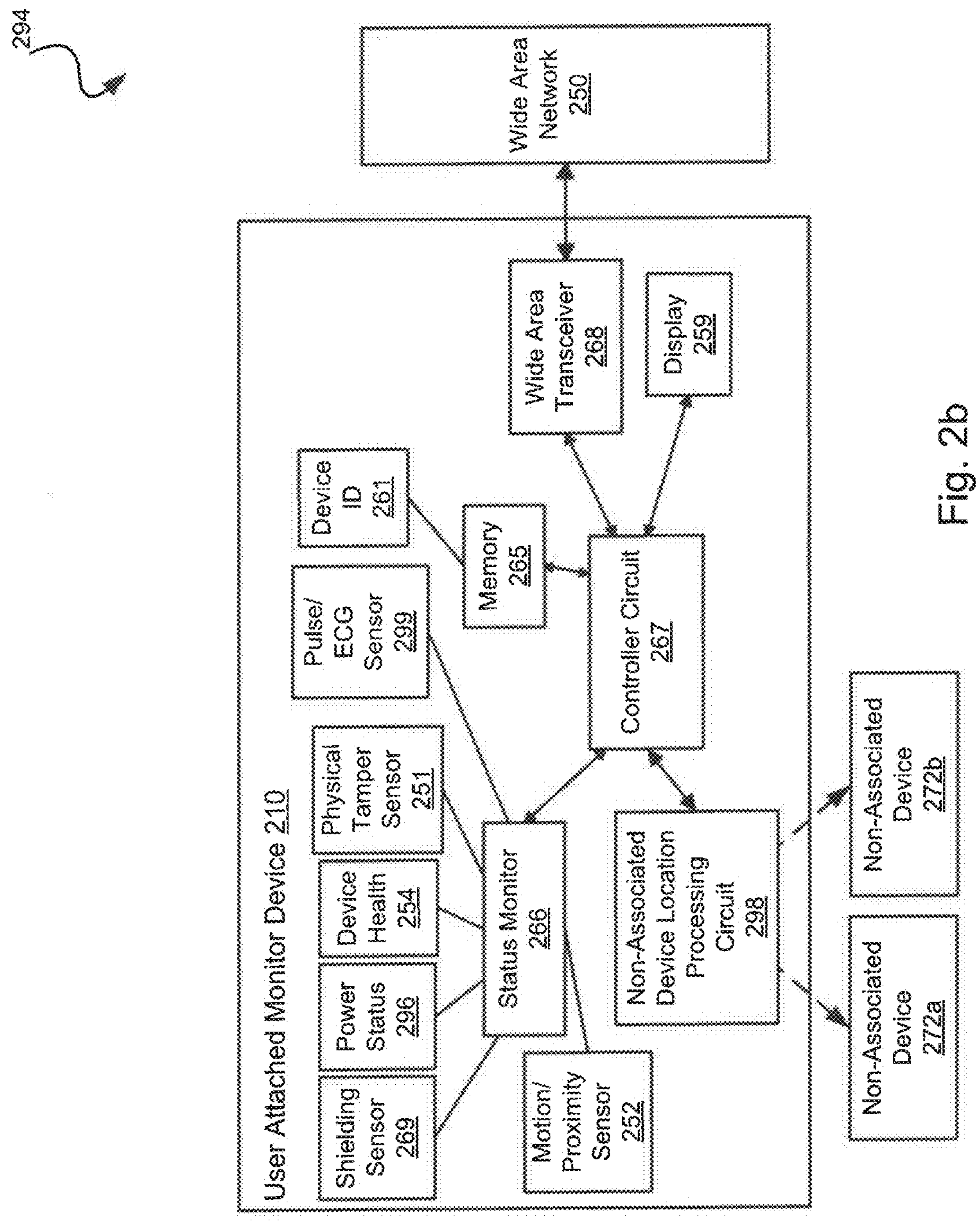

Turning to FIG. 2*b*, a block diagram 294 of user attached monitor device 210 is shown in accordance with some embodiments. As shown, user attached monitor device 210 includes a device ID 261 that may be maintained in a memory 265, and is thus accessible by a controller circuit 267. In some cases, memory 265 may include non-transient instructions (e.g., software-based or firmware-based instructions) executable by controller circuit 267 to perform and/or enable various functions associated with user attached monitor device 210.

User attached monitor device 210 includes a non-associated device location processing circuit 298. Non-associated device location processing circuit 298 is configured to sense that one or more non-associated devices 272 is/are within range of user attached monitor device 210, and to communicate (i.e., transmit) an identification of user attached monitor device 210 to the identified non-associated device. In turn, the non-associated device that received the identification information from user attached monitor device 210 reports the identification received from user attached monitor device 210 and the location of the non-associated device to third-party location reporting system 270. In turn, third-party location reporting system 270 transfers the received identification and location information to a recipient registered with the received identification in the system. In this case, the recipient registered with the received identification in the system is central monitoring station 260. As discussed above, the non-associated devices 272 may be, but are not limited to, mobile telephones, smart watches, or the like that are accessible to third-party location reporting system 270. In one particular embodiment, the combination of non-associated devices 272 and third-party location reporting system 270 are included in the crowd sourced location system provided by Apple™ Based upon the disclosure provided herein, one of ordinary skill in the art will recognize a variety of devices that may be used as non-associated devices, and a variety of systems that may include both non-associated devices and a third-party reporting system used for identifying the location of devices providing identifications to non-associated devices.

When triggered by particular conditions in user detached monitor device 210, controller circuit 267 causes non-associated device location processing circuit 298 to provide for location of user attached monitor device by transmitting its identification to any non-associated device 272 within range. Such conditions and locating operation is discussed more fully in relation to FIGS. 4-8 below.

Various embodiments of user attached monitor device 210 include a variety of sensors capable of determining the status of user attached monitor device 210, and of the individual associated therewith. For example, a status monitor 266 may include one or more of the following subcomponents: power status sensor 296 capable of indicating a power status of user attached monitor device 210, and/or a pulse/ECG sensor 299 operable to sense pulse rate of the monitored individual and an electrocardiogram unique to the monitored individual based upon electrodes (not shown) in contact with the skin of the monitored individual. The power status may be expressed, for example as a percentage of battery life remaining. Based upon the disclosure provided herein, one of ordinary skill in the art will recognize a variety of forms in which power status may be expressed. The pulse rate may be expressed in beats per minute and the ECG may be shown visually via display 259. Based upon the disclosure provided herein, one of ordinary skill in the art will recognize a variety of forms in which pulse rate and/or ECG rate may be expressed.

In addition, user attached monitor device 210 includes a set of shielding sensors 269 that are capable of determining whether user attached monitor device 210 is being shielded from receiving wireless communications, a set of device health indicators 254, a tamper sensor 251 capable of determining whether unauthorized access to user attached monitor device 210 has occurred or whether user attached monitor device 210 has been removed from an associated individual being monitored, and/or a motion/proximity sensor 252 capable of determining whether user attached monitor device 210 is moving and/or whether it is within proximity of an individual associated with user detached monitor device (not shown—see FIG. 3) associated with the monitored individual. In some cases, motion/proximity sensor 252 includes one or more accelerometer sensors and/or vibration gyro sensors that are capable of accurately sensing motion of the monitored individual. In addition, motion/proximity sensor 252 includes sensors capable of determining a proximity of user attached monitor device 210 to a monitored individual to which the device is assigned. This information may be used to assure that the monitored individual is wearing user attached monitor device 210. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into user attached monitor device 210 according to various different instances and/or embodiments.

In some embodiments, a user input (not shown) may be integrated into a display 250 and allows for a user of user attached monitor device 210 to provide information to user attached monitor device 210. Display 259 is communicatively coupled to controller circuit 267.

Figure 3:
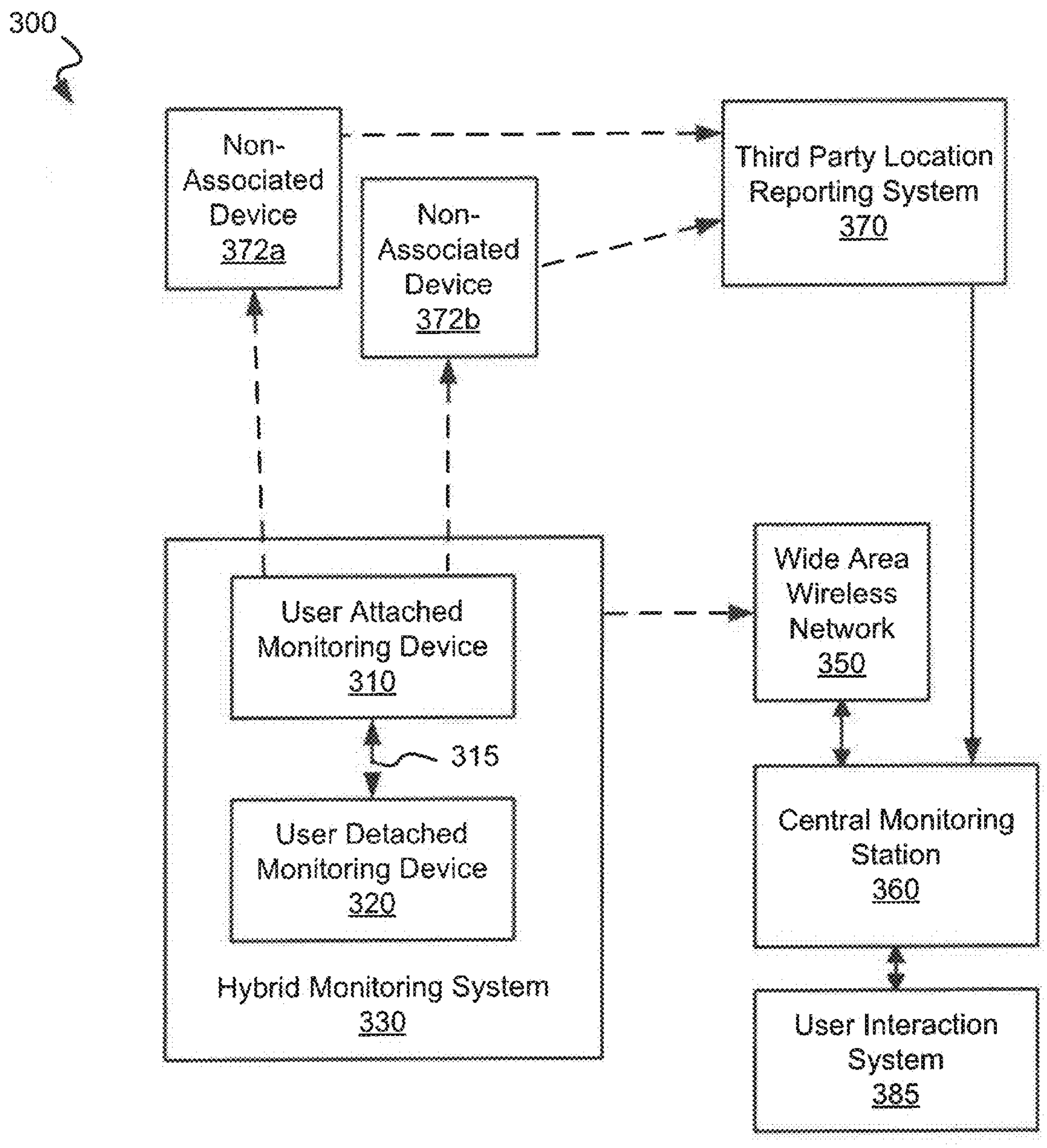
FIG. 3 is a block diagram of a location monitoring system including a hybrid monitoring system capable of establishing location using one or more of WiFi access point-based location determination circuitry, satellite-based location determination circuitry, and/or non-associated device-based location determination circuitry in accordance with various embodiments.

Turning to FIG. 3, a block diagram is shown of a location monitoring system 300 including a hybrid monitoring system 330 capable of establishing location using one or more of WiFi access point-based location determination circuitry, satellite-based location determination circuitry, and/or non-associated device-based location determination circuitry in accordance with various embodiments. Hybrid monitoring system 330 includes both a user attached monitor device 310 and a user detached monitor device 320. User attached monitor device 310 is similar to either user attached monitor device 110 or user attached monitor device 210. Hybrid monitoring system 330 is configured to establish a proxy location using one or more non-associated devices 372 and a third party location reporting system 370 similar to that discussed above in relation to FIGS. 1-2.

User detached monitor device 320 is portable, and may be any device that is recognized as being used by or assigned to an individual being monitored, but is not physically attached to the individual being monitored by a tamper evident attaching device. User detached monitor device 120 may be, but is not limited to, a cellular or mobile telephone configured to communicate with user attached monitor device 310 via a local communication link 315. In contrast, user attached monitor device 310 is attached to the individual being monitored using a tamper evident attaching device like a strap. User attached monitor device 310 may be, but is not limited to, a tracking device that is attached around the limb of an individual and includes indicators to monitor whether the device has been removed from the individual or otherwise tampered.

Location monitoring system 300 further includes a central monitoring station 360 wirelessly coupled to user attached monitor device 310 and/or user detached monitor device 320 via one or more wide area wireless (e.g., cellular telephone network, Internet via a Wi-Fi access point, or the like) communication networks 350.

User detached monitor device 320 includes a location sensor that senses the location of the device and generates a location data. The location data may comprise one or more of: global positioning system ("GPS") data, Assisted GPS ("A-GPS") data, Advanced Forward Link Trilateration ("AFLT") data, and/or cell tower triangulation data. The aforementioned location data is utilized verify the location of a user associated with user detached monitor device 320 at various points as more fully discussed below. User detached monitor device 320 is considered "ambiguous" because it is not attached to the user in a tamper resistant/evident way, but rather is freely severable from the user and thus could be used by persons other than the target. Various processes discussed herein mitigate the aforementioned ambiguity to yield a reasonable belief that information derived from user detached monitor device 320 corresponds to the target.

The location data and/or other data gathered by user detached monitor device 320 may be wirelessly transmitted to central monitoring station 360 via wide area wireless network. Central monitoring station 360 may be any location, device or system where the location data is received, including by way of non-limiting example: a cellular/smart phone, an email account, a website, a network database, and a memory device. The location data is stored by central monitoring station 360 and is retrievable therefrom by a monitor, such as a parent, guardian, parole officer, court liaison, spouse, friend, or other authorized group or individual. In this manner, monitor is able to respond appropriately to the detected out-of-bounds activity by a user. In some cases, the monitor is able to retrieve the location data via a user interaction system 185 which may be, but is not limited to, a network connected user interface device communicatively coupled via a network to central monitoring station 360 and/or directly to user detached monitor device 320 via wide area wireless network 350.

User detached monitor device 320 may further include a user identification sensor operable to generate user identification data for identifying the user in association with the generation of the location data. The user identification data may comprise one or more of: image data, video data, biometric data (e.g. fingerprint, DNA, retinal scan, etc. data), or any other type of data that may be used to verify the identity of the user at or near the time the location data is generated. And the user identification sensor may comprise one or more of: a camera, microphone, heat sensor, biometric data sensor, or any other type of device capable of sensing/generating the aforementioned types of user identification data.

The user identification data is wirelessly transmitted in association with the location data to central monitoring station 360 via a wireless transmitter communicatively coupled to the user identification sensor. The user identification data is stored in association with the location data by central monitoring station 360 and is retrievable therefrom by a monitor, such as a parent, guardian, parole officer, court liaison, spouse, friend, or other authorized group or individual. The monitor is configured to retrieve the location data via a network connected user interface device communicatively coupled—via the network—to central monitoring station 360 and/or to user detached monitor device 320. The location data may be transmitted to central monitoring station 360 independent of the user identification data, for example, during a periodic check-in with central monitoring system 360.

User detached monitor device 320 may further comprise a memory communicatively coupled to a control unit—which is also communicatively coupled to the location sensor, the identification sensor and the wireless transceiver—for controlling the operations thereof in accordance with the functionalities described herein. The memory may include instructions (e.g., software of firmware based instructions) executable by the control unit to perform and/or enable various functions associated with user detached monitor device 320. As user detached monitor device 320 is portable, each of the components may be located within, immediately adjacent to, or exposed without, a device housing whose dimensions are such that user detached monitor device 320 as a whole may be discretely carried by the user, for example, within a pocket or small purse.

Figure 4:
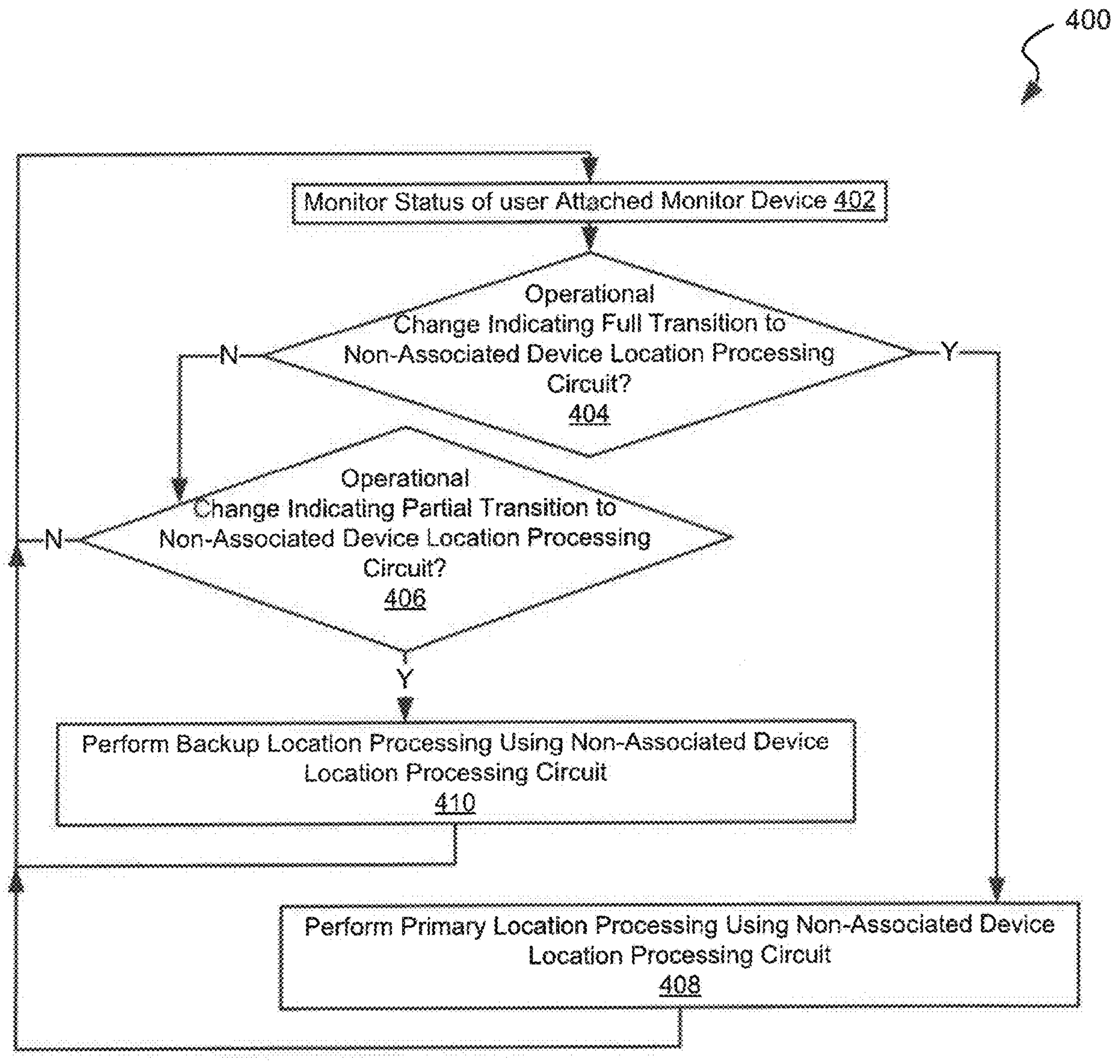
FIG. 4 is a flow diagram showing a method in accordance with some embodiments for utilizing non-associated device-based location in relation to other location methods.

Turning to FIG. 4, a flow diagram 400 shows a method in accordance with some embodiments for utilizing non-associated device-based location in relation to other location methods. Following flow diagram 400, the status of a user attached monitor device is monitored (block 402). This can include monitoring one or more status sensors included in the user attached monitor device. Such status sensors may include, but are not limited to, a power status sensor, a shielding sensor, a device health sensor, a physical tamper sensor, a motion/proximity sensor, and/or a pulse/ECG sensor. Data from one or more of the monitored status sensors is used to determine whether the user attached monitor device has experienced an operational change that would indicate transitioning to location determination based exclusively on non-associated device-based location processing (block 404). One embodiment of implementing the processes of block 404 is discussed below in relation to FIG. 5.

Where it is determined that the user attached monitor device has experienced an operational change that would indicate transitioning to location determination based exclusively on non-associated device-based location processing (block 404), primary location processing using a non-associated device location processing circuit included in the user attached monitor device is performed (block 408). One embodiment showing a method for performing the processes of block 408 is discussed below in relation to FIG. 6.

Alternatively, where it is determined that the user attached monitor device has not experienced an operational change that would indicate transitioning to location determination based exclusively on non-associated device-based location processing (block 404), it is determined whether the user attached monitor device has experienced an operational change that would indicate transitioning to location determination based both upon non-associated device-based location processing and one or more other location processing methods supported by the user attached monitor device (block 406). One embodiment of implementing the processes of block 406 is discussed below in relation to FIG. 7.

Where it is determined that the user attached monitor device has experienced an operational change that would indicate transitioning to location determination based both upon non-associated device-based location processing and one or more other location processing methods supported by the user attached monitor device (block 406), backup location processing using a non-associated device location processing circuit included in the user attached monitor device is performed (block 410). Such backup processing may be selected where location information for a user attached monitor device derived from a WiFi location source has been received over a long period of time. In some cases, such a WiFi location source is a beacon that is deployed at a residence or workplace of an individual to which the user attached monitor device is attached.

When the user attached monitor device comes within range of the beacon which emits a location signal via a WiFi transmission, the user attached monitor device may turn off all GNSS based location circuitry to save power. Some such beacons are plugged in but some operate on battery power, and the beacon has a motion sensor within it. If the motion sensor is tripped, the user attached monitor device re-awakens GNSS location circuitry. However, it may be possible to spoof the WiFi signal or modify the beacon such that it can be moved and yet still report the location where the WiFi source is expected to be. In such a situation it may be desirable to obtain secondary location information using non-associated device processing to confirm the location provided by the WiFi source is accurate. In such a situation, a questionable location information flag may be set causing the user attached monitor device to communicate with one or more non-associated devices within range to perform location processing. In such a case, the location information reported by the non-associated device via a third-party location reporting system can be compared with the location information being reported by the WiFi location circuit of the user attached monitor device to assure that the location of the WiFi source is being reported properly.

Figure 5:
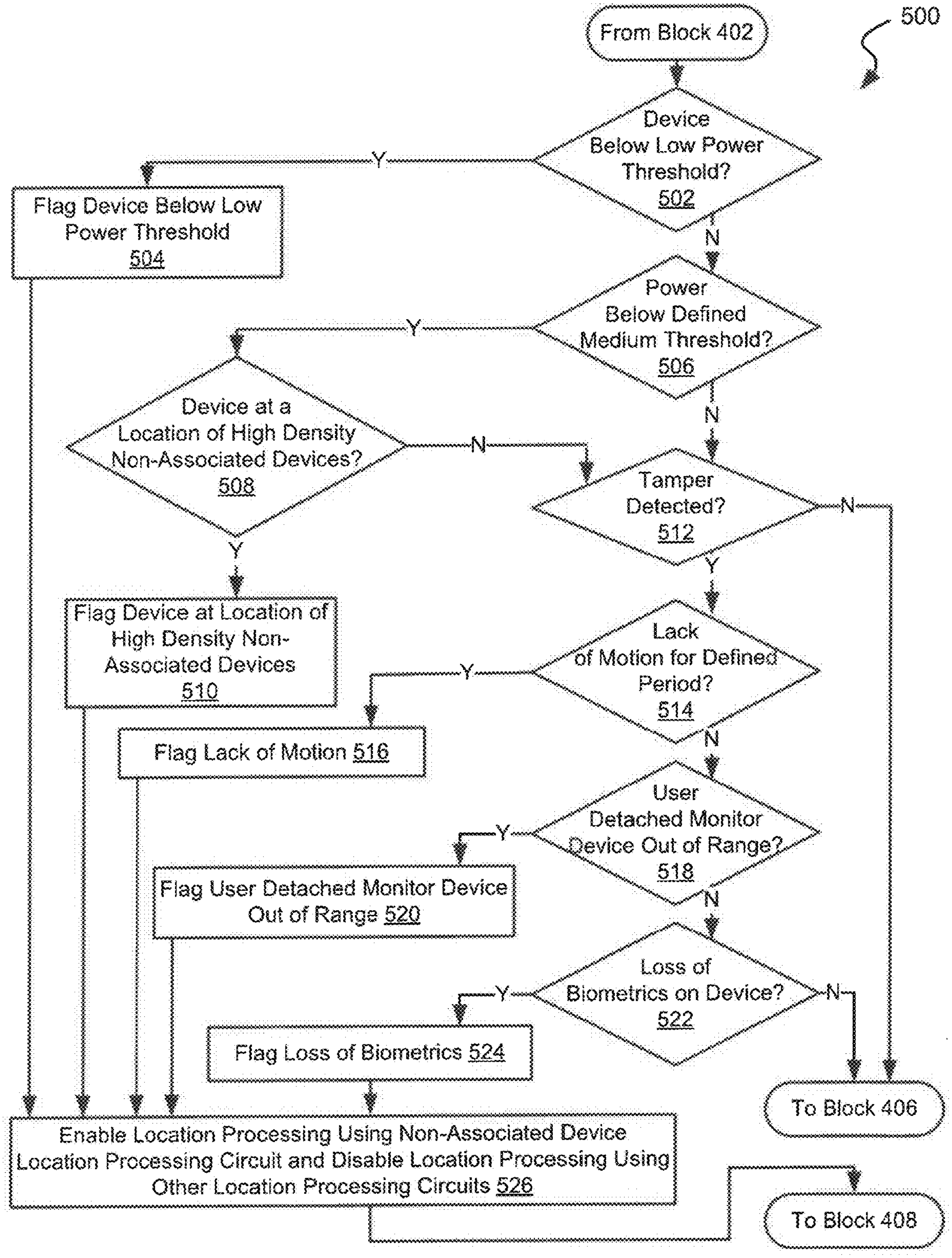
FIGS. 5 and 7 are flow diagrams showing methods in accordance with various embodiments for determining an operational change leading to the use of non-associated device-based location processing.

Turning to FIG. 5, a flow diagram 500 shows a method in accordance with various embodiments for determining an operational change in a user attached monitor device leading to the use of non-associated device-based location processing. Flow diagram 500 begins from block 402 of FIG. 4 and evaluates various monitored data related to the user attached monitor device to determine if a condition has been met to transition the user attached monitor device to using location from non-associated devices as the primary source of location information for the user attached monitor device. Following flow diagram 500, it is determined whether the power source in the user attached monitor device has gone below a low-power threshold (block 502). The low-power threshold may be, for example, a defined percentage of battery life or a time which the device can continue operating on the current charge. This low-power threshold may be user programmable. Based upon the disclosure provided herein, one of ordinary skill in the art will recognize a variety of power thresholds that may be used as the low-power threshold.

Where the power has gone below the low-power threshold (block 502), a below low-power threshold flag is set in the memory of the user attached monitor device (block 504). In addition, location processing using a non-associated device location processing circuit of the user attached monitor device is enabled, and location processing using any of the other location processing circuitry (e.g., WiFi or GPS) is disabled (block 526). In such a situation, the power used by the user attached monitor device is greatly reduced. In addition, the below low-power threshold flag has been set and will remain set until the power of the user attached monitor device is significantly increased as discussed below in relation to FIG. 6, and the processing continues in block 408 of FIG. 4.

Alternatively, where the power has not gone below the low-power threshold (block 502), it is determined whether the power source in the user attached monitor device has gone below a medium power threshold (block 506). The medium power threshold may be, for example a defined percentage of a battery life or a time which the device can continue operating on the current charge. This low-power threshold may be user programmable. Based upon the disclosure provided herein, one of ordinary skill in the art will recognize a variety of power thresholds that may be used as the medium power threshold.

Where the power has gone below the medium power threshold (block 506), it is determined whether the user attached monitor device is currently in a location with a high density of non-associated devices that can be relied upon to transmit location data for the user attached monitor device (block 508). Locations with a high density of non-associated devices may be airports, shopping centers, sports or entertainment venues, or other locations where a large number of people with mobile devices are expected to be. Alternatively, locations with a high density of non-associated devices may be discerned in real time by the user attached monitor device where the user attached monitor device detects at least a defined number of non-associated devices within communication range. Based upon the disclosure provided herein, one of ordinary skill in the art will recognize a variety of approaches for identifying locations with a high density of non-associated devices.

Where it is determined that the power has gone below the medium power threshold (block 506) and the user attached monitor device is operating in a location with a high density of non-associated devices (block 508), a location with a high density of non-associated devices flag is set in the memory of the user attached monitor device (block 510). In addition, location processing using the non-associated device location processing circuit of the user attached monitor device is enabled, and location processing using any of the other location processing circuitry (e.g., WiFi or GPS) is disabled (block 526). In such a situation, the power used by the user attached monitor device is greatly reduced, and the location with a high density of non-associated devices flag has been set and will remain set until either the power of the user attached monitor device is significantly increased or the user attached monitor device moves away from the location with the high density of non-associated devices as discussed below in relation to FIG. 6, and the processing continues in block 408 of FIG. 4.

Alternatively, where it is either determined that the power has not gone below the medium power threshold (block 506) or that the user attached monitor device is not currently in a location with a high density of non-associated devices that can be relied upon to transmit location data for the user attached monitor device (block 508), it is determined whether a tamper has been detected (block 512). A tamper may be any indication that the user attached monitor device has been improperly accessed. Such a tamper may include, but is not limited to, an attempt to remove the user attached monitor device from the monitored individual. As one example, a tamper is indicated when the strap attaching the user attached monitor device to the monitored individual is cut. Based upon the disclosure provided herein, one ordinary skill in the art will recognize a variety of tamper detection circuits that may be used to detect a tamper and a variety of different occurrences where a tamper would be indicated in relation to different embodiments.

Where it is determined that a tamper has been detected (block 512), it is determined whether a lack of motion of the user attached monitor device has occurred (block 514). This lack of motion may be detected, for example, using a motion/proximity sensor included in the user attached monitor device. Detection of a lack of motion after detection of a tamper suggests the possibility that the user attached monitor device has been removed from the monitored individual and discarded. In such a case, a lower power approach to determining the location of the user attached monitor device is important to allow time for the device to be recovered.

Where it is determined that a tamper has been detected (block 512) along with a lack of motion of the user detached monitor device (block 514), a lack of motion flag is set in the memory of the user attached monitor device (block 516). In addition, location processing using the non-associated device location processing circuit of the user attached monitor device is enabled, and location processing using any of the other location processing circuitry (e.g., WiFi or Satellite) is disabled (block 526). In such a situation, the power used by the user attached monitor device is greatly reduced, and the lack of motion flag has been set and will remain set until either the tamper is resolved or motion indicative of attachment of the user attached monitor device to the monitored individual is detected as discussed below in relation to FIG. 6, and the processing continues in block 408 of FIG. 4.

Alternatively, where it is determined that a tamper has been detected (block 512), but motion of the user attached monitor device is continuing (block 514), it is determined whether the user attached monitor device is out of range of a user detached monitor device associated with the monitored individual (block 518). This determination is only made where a hybrid monitoring system is being used. This lack of communication or contact between the user attached monitor device and the user detached monitor device suggests a possibility that the detected tamper related to the user attached monitor device has been removed from the monitored individual, and the monitored individual has carried the user detached monitor device away from the user attached monitor device. In such a case, a lower power approach to determining the location of the user attached monitor device is important to allow time for the device to be recovered.

Where it is determined that a tamper has been detected (block 512) along with a loss of communication with the user detached monitor device (block 518), a user detached monitor device out of range flag is set in the memory of the user attached monitor device (block 520). In addition, location processing using the non-associated device location processing circuit of the user attached monitor device is enabled, and location processing using any of the other location processing circuitry (e.g., WiFi or Satellite) is disabled (block 526). In such a situation, the power used by the user attached monitor device is greatly reduced, and the user detached monitor device out of range flag has been set and will remain set until either the tamper is resolved or the user detached monitor device again starts communicating with the user attached monitor device as discussed below in relation to FIG. 6, and the processing continues in block 408 of FIG. 4.

Alternatively, where it is determined that a tamper has been detected (block 512), and the user detached monitor device remains in range of the user attached monitor device (block 518), it is determined whether the biometrics of the monitored individual are still registering with the user attached monitor device (block 522). Such biometrics may include, but are not limited to, pulse and/or ECG of the monitored individual. This lack of biometrics may be detected, for example, using a pulse/ECG sensor included in the user attached monitor device. Detection of a lack of biometrics after detection of a tamper suggests the possibility that the user attached monitor device has been removed from the monitored individual and discarded. In such a case, a lower power approach to determining the location of the user attached monitor device is important to allow time for the device to be recovered.

Where it is determined that a tamper has been detected (block 512) along with a loss of biometrics (block 522), a loss of biometrics flag is set in the memory of the user attached monitor device (block 524). In addition, location processing using the non-associated device location processing circuit of the user attached monitor device is enabled, and location processing using any of the other location processing circuitry (e.g., WiFi or Satellite) is disabled (block 526). In such a situation, the power used by the user attached monitor device is greatly reduced, and the loss of biometrics flag has been set and will remain set until either the tamper is resolved or the biometrics are again sensed by the user attached monitor device as discussed below in relation to FIG. 6, and the processing continues in block 408 of FIG. 4. Where a tamper has not been detected (block 512) or none of the additional conditions are met (blocks 514, 518, 522), processing returns to block 406 of FIG. 4.

Figure 6:
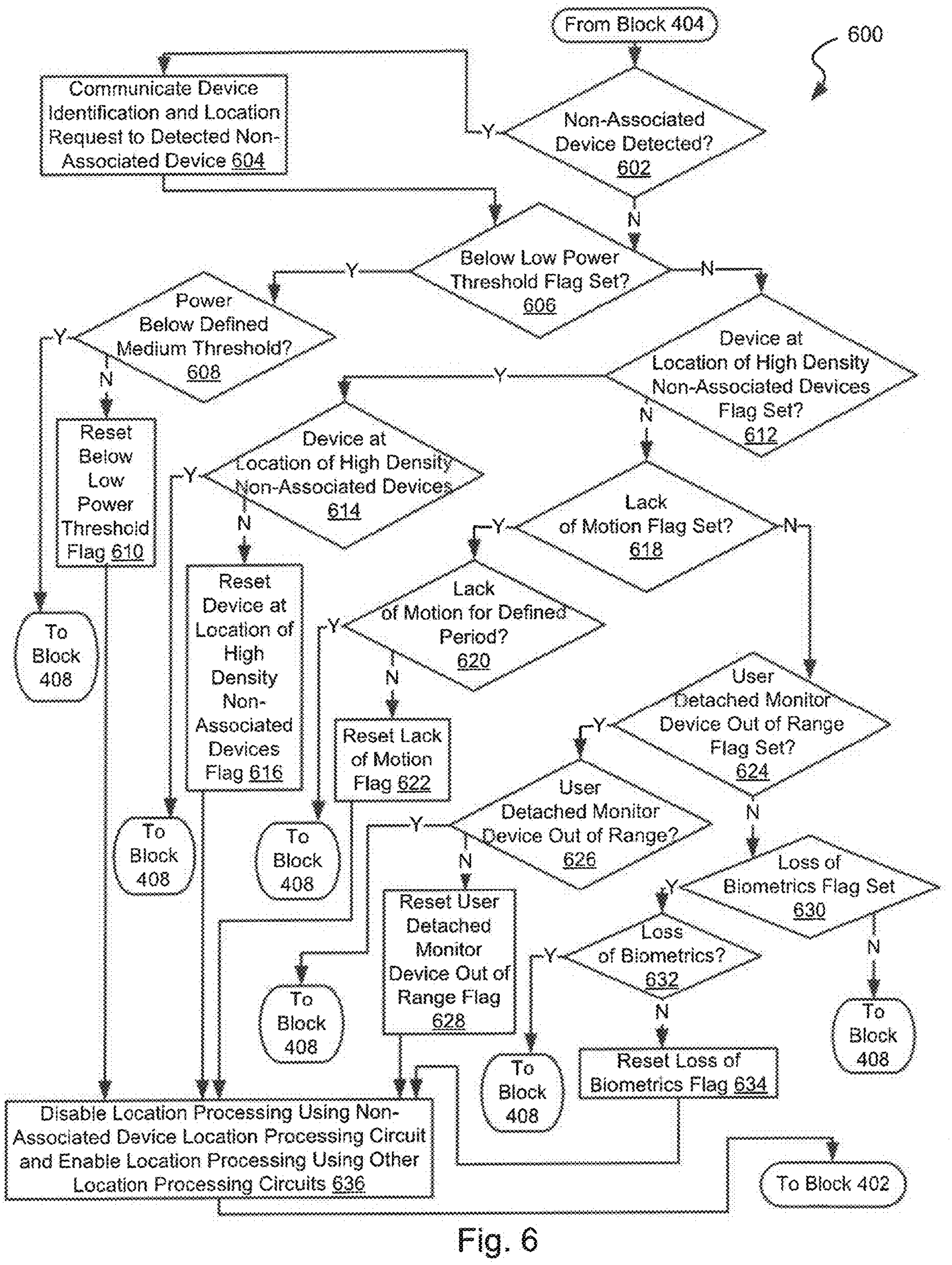
FIGS. 6 and 8 are flow diagrams showing methods in accordance with some embodiments for performing non-associated device-based location processing.

Turning to FIG. 6, a flow diagram 600 shows a method in accordance with various embodiments for performing non-associated device-based location processing. Flow diagram 600 begins from block 404 of FIG. 4 and performs primary location processing using non-associated device location processing circuitry of the user attached monitor device. Following flow diagram 600, it is determined whether a non-associated device has been detected (block 602). A low-power communication protocol such as, for example, BlueTooth™ may be used by a non-associated device location processing circuit of the user attached monitor device to ping for any non-associated devices within communication range. Where a non-associated device is within communication range, the non-associated device location processing circuit indicates detection of a non-associated device.

Where a non-associated device is detected (block 602), the device identification of the user attached monitor device is communicated to the identified non-associated device with, in some cases, a request for the non-associated device to forward the device identification along with the location of the non-associated device to a third-party location reporting system (block 604). In one embodiment, the non-associated devices are configured to provide tracking information via a third-party location reporting system included as part of the crowd sourced location system provided by Apple™.

It is determined whether the below low-power threshold flag is set (block 606). This flag is set whenever the reason for communicating location information via the non-associated devices was triggered due to a low-power condition in the user attached monitor device as discussed above in relation to block 504 of FIG. 5. Where the below low-power threshold flag is set (block 606), it is determined whether the low-power condition of the user attached monitor device still exists or whether the user attached monitor device has been recharged (block 608).

Where the low-power condition no longer exists (block 608), the below low-power threshold flag is reset (block 610), and the location processing using the non-associated device location processing circuit is disabled and location processing using one or more other location processing circuits in the user attached monitor device are re-enabled (block 636). Said another way, the user attached monitor device is returned to its pre-power loss operational status. With the below low-power threshold flag reset (block 610) and the operational status of the user attached monitor device returned (block 636), the process returns to block 402 of FIG. 4. Alternatively, where the low-power condition still exists (block 608), the processing returns to block 408 of FIG. 4 where use of the non-associated devices for location continues.

Alternatively, where the below low-power threshold flag is not set (block 606), it is determined whether the high density of non-associated devices flag is set in the memory of the user attached monitor device (block 612). This flag is set whenever the reason for communicating location information via the non-associated devices was triggered due to a high density of non-associated device as discussed above in relation to block 510 of FIG. 5. Where the high density of non-associated devices flag is set (block 612), it is determined whether the user attached monitor device is still operating in an area that has a high density of non-associated devices (block 614).

Where the high density of non-associated devices no longer exists (block 614), the high density of non-associated devices flag is reset (block 616), and the location processing using the non-associated device location processing circuit is disabled and location processing using one or more other location processing circuits in the user attached monitor device are re-enabled (block 636). Said another way, the user attached monitor device is returned to its pre-power loss operational status. With the high density of non-associated devices flag reset (block 610) and the operational status of the user attached monitor device returned (block 636), the process returns to block 402 of FIG. 4. Alternatively, where the high density of non-associated devices condition still exists (block 614), the processing returns to block 408 of FIG. 4 where use of the non-associated devices for location continues.

Alternatively, where the high density of non-associated devices flag is not set (block 612), it is determined whether the lack of motion flag is set in the memory of the user attached monitor device (block 618). This flag is set whenever the reason for communicating location information via the non-associated devices was triggered due to a lack of motion of the user attached monitor device as discussed above in relation to block 516 of FIG. 5. Where the lack of motion flag is set (block 618), it is determined whether the user attached monitor device is still not moving (block 620).

Where new motion has been detected in the user attached monitor device (block 620), the lack of motion flag is reset (block 622), and the location processing using the non-associated device location processing circuit is disabled and location processing using one or more other location processing circuits in the user attached monitor device are re-enabled (block 636). Said another way, the user attached monitor device is returned to its pre-power loss operational status. With the lack of motion flag reset (block 622) and the operational status of the user attached monitor device returned (block 636), the process returns to block 402 of FIG. 4. Alternatively, where the lack of motion condition still exists (block 620), the processing returns to block 408 of FIG. 4 where use of the non-associated devices for location continues.

Alternatively, where the lack of motion flag is not set (block 618), it is determined whether the user detached monitor device out of range flag is set in the memory of the user attached monitor device (block 6624). This flag is set whenever the reason for communicating location information via the non-associated devices was triggered due to a lack of communication with the user detached monitor device associated with the monitored individual as discussed above in relation to block 520 of FIG. 5. Where the user detached monitor device out of range flag is set (block 624), it is determined whether the user attached monitor device is still out of range of the user detached monitor device (block 626).

Where new communication with the user detached monitor device has been established (block 626), the user detached monitor device out of range flag is reset (block 628), and the location processing using the non-associated device location processing circuit is disabled and location processing using one or more other location processing circuits in the user attached monitor device are re-enabled (block 636). Said another way, the user attached monitor device is returned to its pre-power loss operational status. With the user detached monitor device out of range flag reset (block 628) and the operational status of the user attached monitor device returned (block 636), the process returns to block 402 of FIG. 4. Alternatively, where the user detached monitor device out of range condition still exists (block 626), the processing returns to block 408 of FIG. 4 where use of the non-associated devices for location continues.

Alternatively, where the user detached monitor device out of range flag is not set (block 624), it is determined whether the loss of biometrics flag is set in the memory of the user attached monitor device (block 630). This flag is set whenever the reason for communicating location information via the non-associated devices was triggered due to a lack of biometrics sensed by the user attached monitor device as discussed above in relation to block 524 of FIG. 5. Where the loss of biometrics flag is set (block 630), it is determined whether the loss of biometrics condition continues (block 632).

Where new biometrics are sensed by the user attached monitor device (block 632), the loss of biometrics flag is reset (block 634), and the location processing using the non-associated device location processing circuit is disabled and location processing using one or more other location processing circuits in the user attached monitor device are re-enabled (block 636). Said another way, the user attached monitor device is returned to its pre-power loss operational status. With the loss of biometrics flag reset (block 634) and the operational status of the user attached monitor device returned (block 636), the process returns to block 402 of FIG. 4. Alternatively, where the loss of biometrics condition continues (block 634), the processing returns to block 408 of FIG. 4 where use of the non-associated devices for location continues.

Figure 7:
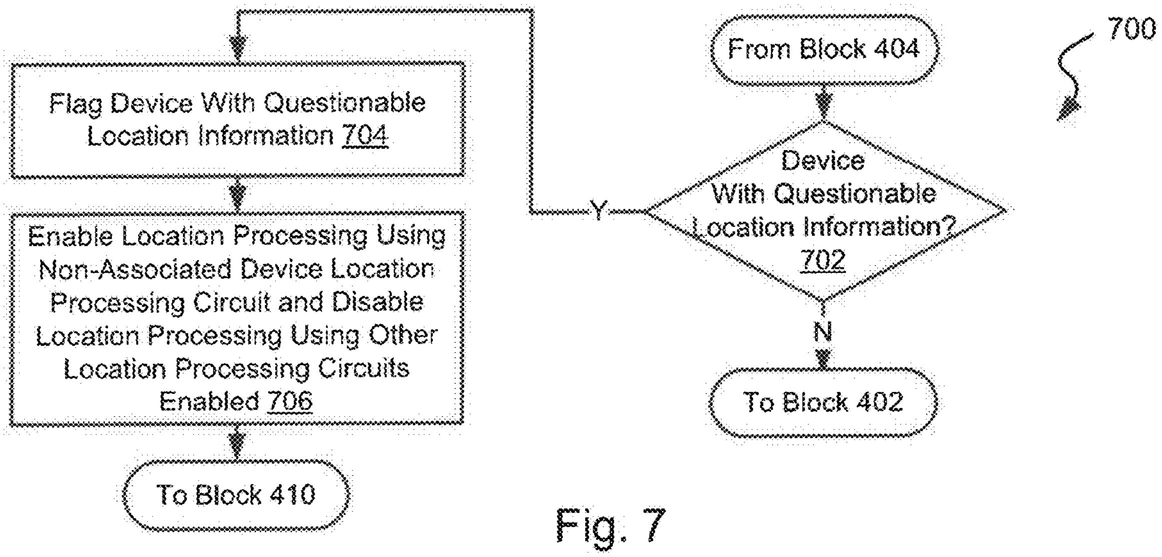

Turning to FIG. 7, a flow diagram 700 shows another method in accordance with various embodiments for determining an operational change leading to the use of non-associated device-based location processing. Flow diagram 700 begins from block 404 of FIG. 4 and evaluates various monitored data related to the user attached monitor device to determine if a condition has been met to transition the user attached monitor device to using location from non-associated devices as the exclusive source of location information for the user attached monitor device. Following flow diagram 700, it is determined whether one or more location circuits of the user attached monitor device is providing questionable location information (block 702). Location information from the user attached monitor device may be considered questionable for any of a number of reasons including, without limitation, successively reported location points indicating that the user attached monitor device is moving faster than is possible, a reported location point that is unlikely due to one or more reasons, or location information being reported when the location of the user attached monitor device is at a location where it is difficult to get accurate location information (e.g., in a building). Based upon the disclosure provided herein, one of ordinary skill in the art will recognize a variety of conditions which would cause the location information reported by the user attached monitor device to be considered questionable.

Where the location information from the user attached monitor device is considered questionable (block 702), a questionable location information flag is set in the memory of the user attached monitor device (block 704). In addition, location processing using a non-associated device location processing circuit of the user attached monitor device is enabled at the same time that location processing using any of the other location processing circuitry (e.g., WiFi or Satellite) is disabled (block 706). The processing then continues with block 410 of FIG. 4. Alternatively, where the location information from the user attached monitor device is not considered questionable (block 702), processing returns to block 402 of FIG. 4.

Figure 8:
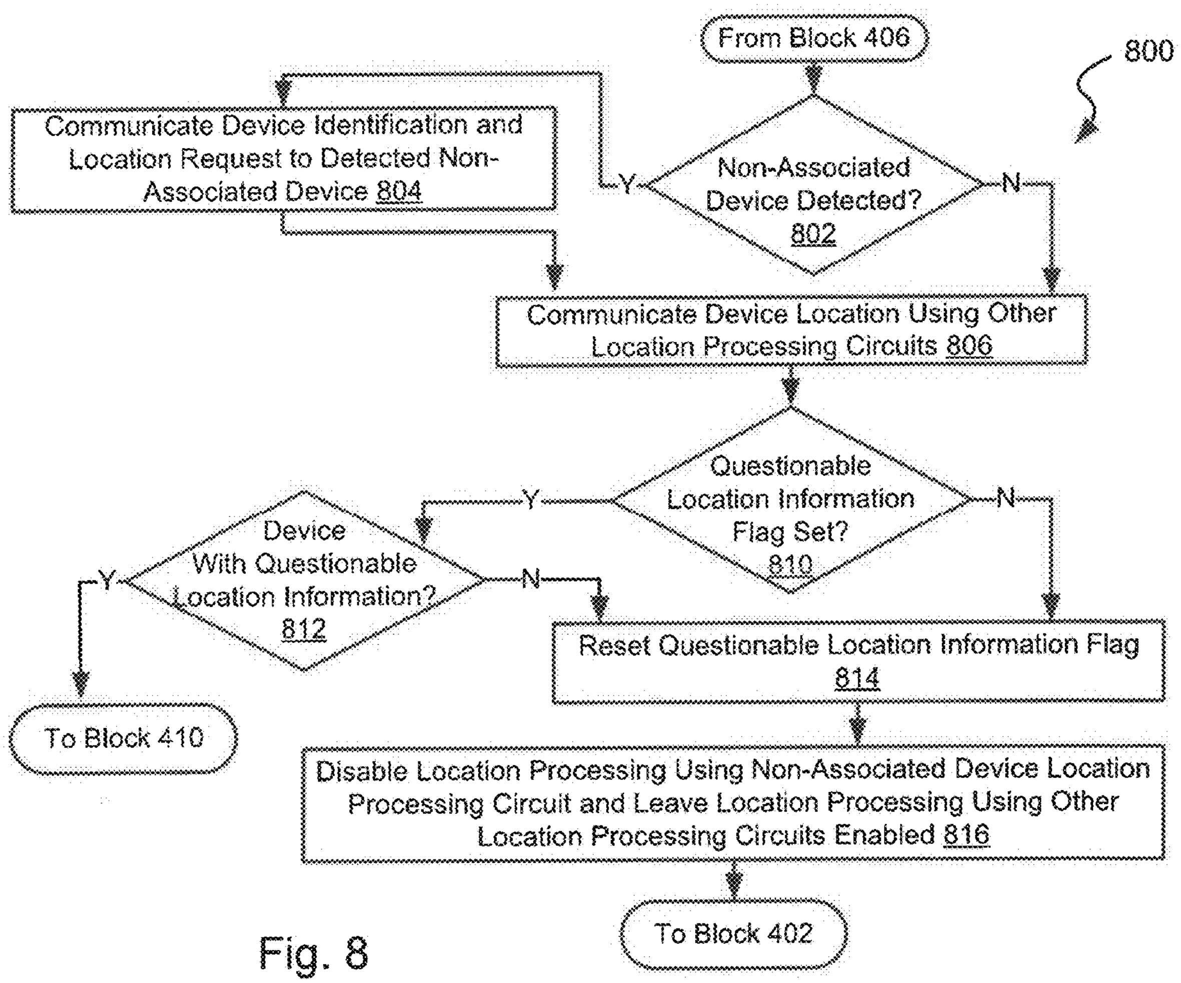

Turning to FIG. 8, a flow diagram 800 shows another method in accordance with various embodiments for determining an operational change leading to the use of non-associated device-based location processing. Flow diagram 800 begins from block 406 of FIG. 4 and determines if a non-associated device is within communication range of a user attached monitor device (block 802). Where a non-associated device is within communication range of a user attached monitor device (block 802), user attached monitor device communicates its identification and a location request to the non-associated device (block 804). In addition, device location is communicated to a central monitoring system using one of the other location circuits (e.g., WiFi or GPS) available in the user attached monitor device (block 806).

It is determined whether a questionable location information flag has been set (block 810). Where a questionable location information flag has been set (block 810), it is determined whether the user attached monitor device is returning questionable location information (block 812). Where either the user attached monitor device is not returning questionable location information (block 812) or the questionable location information flag is not set (block 810), the questionable location information flag is reset (block 814). At this juncture, location processing using non-associated device location processing is disabled and location processing using location circuitry in the user attached monitor device remains enabled (block 816). Processing returns to block 402 of FIG. 4.

In conclusion, the present invention provides for novel systems, devices, and methods for providing location information for a tracking device. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method for tracking, the method comprising:

monitoring an operational status of a monitoring device to yield at least a first operational status of the monitoring device;

based at least in part on the first operational status of the monitoring device, enabling a non-associated device-based location processing in the monitoring device, wherein the non-associated device-based location processing includes:

communicating a data set identifying the monitoring device to a non-associated device within communication range of the monitoring device, wherein a location of the non-associated device is used as a proxy for a location of the monitoring device; and reporting the location of the non-associated device as a location of the monitoring device to a recipient device.

2. The method of claim 1, wherein the non-associated device is a mobile phone associated with a third-party location service.

3. The method of claim 1, wherein the monitoring device is a user attached monitoring device including a securing mechanism configured to secure the user attached monitoring device to a monitored individual.

4. The method of claim 1, wherein the monitoring device is a user attached monitoring device, wherein the user attached monitoring device is configured to perform direct location processing, and wherein the direct location processing is selected from a group consisting of: satellite-based location processing, and WiFi based location processing.

5. The method of claim 4, the method further comprising: based at least in part on the first operational status of the monitoring device, disabling the direct location processing.

6. The method of claim 1, wherein the first operational status of the monitoring device is selected from a group consisting of: a power status of the monitoring device, and a tamper status of the monitoring device.

7. The method of claim 1, wherein the first operational status of the monitoring device is a power status of the monitoring device, and wherein enabling the non-associated device-based location processing in the monitoring device is based upon a combination of the power status of the monitoring device and a likelihood that the monitoring device is within communication range of two or more non-associated devices.

8. The method of claim 1, wherein the first operational status of the monitoring device is a tamper status of the monitoring device, and wherein enabling the non-associated device-based location processing in the monitoring device is based upon a combination of the tamper status of the monitoring device and at least one of: a motion status of the monitoring device, or a biometrics status of the monitoring device.

9. The method of claim 1, wherein the first operational status of the monitoring device is a tamper status of the monitoring device, wherein the monitoring device is a user attached monitoring device attached to a monitored individual, and wherein enabling the non-associated device-based location processing in the monitoring device is based upon a combination of the tamper status of the monitoring device and a communication status with a user detached monitoring device associated with the monitored individual.

10. The method of claim 9, wherein the user detached monitoring device is a mobile phone.

11. A tracking system, comprising:

a monitoring device associated with a monitored individual, wherein the monitoring device includes:

a non-associated device-based location processing circuit;

a direct location processing circuit, wherein the direct location processing circuit is selected from a group consisting of: a satellite-based location processing circuit, and WiFi based location processing circuit;

a processor; and a computer readable medium having stored therein instructions which when executed by the processor cause the processor to:

monitor an operational status of the monitoring device to yield at least a first operational status of the monitoring device;

based at least in part on the first operational status of the monitoring device, enable the non-associated device-based location processing circuit in the monitoring device, wherein the non-associated device-based location processing circuit is configured to:

communicate a data set identifying the monitoring device to a non-associated device within communication range of the monitoring device, wherein a location of the non-associated device is used as a proxy for a location of the monitoring device; and rely upon the non-associated device to report a location of the non-associated device as a location of the monitoring device to a recipient device.

12. The tracking system of claim 11, wherein the monitoring device is a user attached monitoring device including a securing mechanism configured to secure the user attached monitoring device to a monitored individual.

13. The tracking system of claim 11, wherein the computer readable medium further has stored therein instructions which when executed by the processor cause the processor to:

disable the direct location processing circuit based at least in part on the first operational status of the monitoring device.

14. The tracking system of claim 11, wherein the first operational status of the monitoring device is selected from a group consisting of: a power status of the monitoring device, and a tamper status of the monitoring device.

15. The tracking system of claim 11, wherein the first operational status of the monitoring device is a power status of the monitoring device, and wherein enabling the non-associated device-based location processing in the monitoring device is based upon a combination of the power status of the monitoring device and a likelihood that the monitoring device is within communication range of two or more non-associated devices.

16. The tracking system of claim 11, wherein the first operational status of the monitoring device is a tamper status of the monitoring device, and wherein enabling the non-associated device-based location processing in the monitoring device is based upon a combination of the tamper status of the monitoring device and at least one of: a motion status of the monitoring device, or a biometrics status of the monitoring device.

17. The tracking system of claim 11, wherein the first operational status of the monitoring device is a tamper status of the monitoring device, wherein the monitoring device is a user attached monitoring device attached to a monitored individual, and wherein enabling the non-associated device-based location processing in the monitoring device is based upon a combination of the tamper status of the monitoring device and a communication status with a user detached monitoring device associated with the monitored individual.

18. The tracking system of claim 17, wherein the user detached monitoring device is a mobile phone.

19. The tracking system of claim 11, further comprising:

a central monitoring station configured to receive location information derived from both of:

the non-associated device, and the direct location processing circuit.

20. The tracking system of claim 19, wherein the central monitoring station is configured to receive location information derived from both of the non-associated device, and the direct location processing circuit concurrently.

* * * * *